United States Patent
Coburn et al.

(10) Patent No.: US 8,741,928 B2
(45) Date of Patent: Jun. 3, 2014

(54) PROTECTED ANTIMICROBIAL COMPOUNDS FOR HIGH TEMPERATURE APPLICATIONS

(75) Inventors: Charles E. Coburn, Vernon Hills, IL (US); Michael V. Enzien, Lisle, IL (US); Heather R. Mcginley, Highland Park, IL (US); David W. Moore, Hebron, IL (US)

(73) Assignees: Dow Global Technologies LLC, Midland, MI (US); ANGUS Chemical Company, Buffalo Grove, IL (US)

( * ) Notice: Subject to any disclaimer, the term of this patent is extended or adjusted under 35 U.S.C. 154(b) by 0 days.

(21) Appl. No.: 13/993,523

(22) PCT Filed: Dec. 2, 2011

(86) PCT No.: PCT/US2011/063074
§ 371 (c)(1),
(2), (4) Date: Jun. 12, 2013

(87) PCT Pub. No.: WO2012/082404
PCT Pub. Date: Jun. 21, 2012

(65) Prior Publication Data
US 2013/0261148 A1    Oct. 3, 2013

Related U.S. Application Data

(60) Provisional application No. 61/424,190, filed on Dec. 17, 2010.

(51) Int. Cl.
*A61K 31/445* (2006.01)
*A61K 31/415* (2006.01)
*A61K 31/40* (2006.01)

(52) U.S. Cl.
USPC ........... 514/320; 514/385; 514/396; 514/413; 514/414

(58) Field of Classification Search
USPC .......................... 514/320, 385, 396, 413, 414
See application file for complete search history.

(56) References Cited

U.S. PATENT DOCUMENTS

| | | |
|---|---|---|
| 5,464,850 A | 11/1995 | Voo et al. |
| 2004/0152749 A1 | 8/2004 | Merianos et al. |
| 2005/0059559 A1 | 3/2005 | Nettleship et al. |
| 2005/0113425 A1 | 5/2005 | Beilfuss et al. |
| 2009/0088483 A1 | 4/2009 | Anker et al. |
| 2010/0078393 A1 | 4/2010 | Yin |

FOREIGN PATENT DOCUMENTS

GB    2382588    6/2004

OTHER PUBLICATIONS

Eachus, et al., "Oxban-e: an alternative preservative for cosmetic and toilteries", Neue Rohstoffe, vol. 116, No. 14 pp. 537-538 (1990).
Zayed, "Reaction of 2-Methyl-2-Amino-1,3-Propan-Diol with Aldehydes and Ketones Synthesis of Oxazolidine and Imidazoline Derivatives Antimicrobial Agents", J. Scientific, pp. 432-438 ((1987).

*Primary Examiner* — Raymond Henley, III
(74) *Attorney, Agent, or Firm* — Tifani M. Edwards

(57) ABSTRACT

Provided are protected antimicrobial compounds which are useful for controlling microorganisms in aqueous or water-containing systems, such as oil or gas field fluids, at elevated temperature. The antimicrobial compounds are of the formula I:

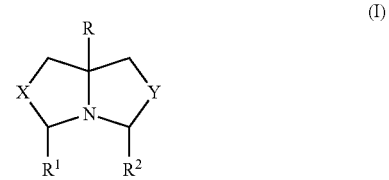

(I)

wherein R, $R_1$, $R_2$, X and Y are as defined herein.

8 Claims, No Drawings

PROTECTED ANTIMICROBIAL COMPOUNDS FOR HIGH TEMPERATURE APPLICATIONS

FIELD OF THE INVENTION

The invention relates to protected antimicrobial compounds and methods of their use for the control of microorganisms in aqueous or water-containing systems.

BACKGROUND OF THE INVENTION

Protecting aqueous systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Various aldehyde compounds, including formaldehyde and glutaraldehyde are known antimicrobials that are used to control the growth of microorganisms in aqueous systems and fluids, including those found in oil and gas operations. The materials, however, are susceptible to a number of drawbacks. For instance, they can degrade over time at the elevated temperatures often encountered in the oil and gas production environment. The materials can also be inactivated by other common oilfield chemicals such as bisulfite salts and amines. These conditions can leave oilfield infrastructure (wells, pipelines, etc.) and formations susceptible to microbial fouling.

It would be an advance in the art if new antimicrobial systems, which provided improved thermal and chemical stability, were developed.

BRIEF SUMMARY OF THE INVENTION

The invention provides methods for controlling microorganisms in aqueous or water-containing systems having a temperature of at least 40° C. The method comprises contacting the aqueous or water-containing system with a protected antimicrobial compound as described herein.

The invention also provides protected antimicrobial compounds that are useful for controlling microorganisms in aqueous or water-containing systems having a temperature of at least 40° C.

DETAILED DESCRIPTION OF THE INVENTION

As noted above, the invention provides compounds and methods of using them for the control of microorganisms in aqueous or water-containing systems, including those found in oil and gas operations. The invention uses protected antimicrobial compounds that release formaldehyde or glutaraldehyde when heat-activated. Unlike the free aldehydes, however, the protected compounds are more stable at elevated temperatures thus permitting extended control of microbial fouling. In addition, the protected compounds may exhibit improved stability in the presence of other chemical species that would otherwise degrade the free aldehydes, such as bisulfites, and amines.

The protected antimicrobial compound for use in the methods described herein may be represented by the formula I:

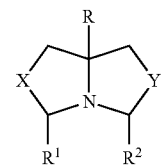

(I)

wherein R is $C_1$-$C_6$ alkyl optionally substituted with hydroxyl; X and Y are independently O or NR" wherein R" is independently H or $C_1$-$C_6$ alkyl; and $R^1$ and $R^2$ are H or $R^1$ and $R^2$, together with the CH—N—CH group to which they are attached, form a piperidinyl ring.

Protected antimicrobial compounds of formula I are suitable for releasing formaldehyde or glutaraldehyde, according to the methods of the invention.

Preferred compounds of formula I include compounds of formula I-1, which are compounds of formula I wherein X and Y are each O.

Preferred compounds of formula I-1 include compounds of formula I-2, which are compounds of formula I-1 wherein $R^1$ and $R^2$, together with the CH—N—CH group to which they are attached, form a piperidinyl ring.

Preferred compounds of formula I include compounds of formula I-3, which are compounds of formula I wherein X and Y are each NR". In some embodiments, X and Y are each NH.

Preferred compounds of formula I-3 include compounds of formula I-4, which are compounds of formula I-3 wherein $R^1$ and $R^2$ are each H.

Preferred compounds of formula I-3 include compounds of formula I-5, which are compounds of formula I-3 wherein $R^1$ and $R^2$, together with the CH—N—CH group to which they are attached, form a piperidinyl ring.

Preferred compounds of formulae I, I-1, I-2, I-3, I-4, and I-5 include compounds of formula I-6, which are compounds of formula I, I-1, I-2, I-3, I-4, or I-5 wherein R is $C_1$-$C_3$ alkyl optionally substituted with one hydroxyl. In some embodiments, R is methyl. In some embodiments, R is ethyl. In some embodiments, R is hydroxymethyl.

Exemplary compounds of formula I include the following:

| Name | Structure |
|---|---|
| 7a-methylhexahydro-1H-imidazo[1,5-c]imidazole | 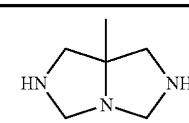 |
| 7a-ethylhexahydro-1H-imidazo[1,5-c]imidazole | 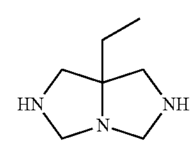 |
| 2a-methyloctahydro-1,4-dioxa-2a1-azacyclopenta[cd]indene | 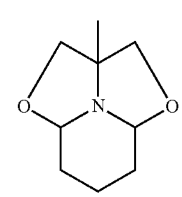 |

| Name | Structure |
|---|---|
| 2a-ethyloctahydro-1,4-dioxa-2a¹-azacyclopenta[cd]indene | |
| (Octahydro-1,4-dioxa-2a¹-azacyclopenta[cd]inden-2a-yl)methanol | |
| 2a-methyldecahydro-1,2a1,4-triazacyclopenta[cd]indene | 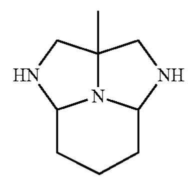 |
| 2a-ethyldecahydro-1,2a1,4-triazacyclopenta[cd]indene | 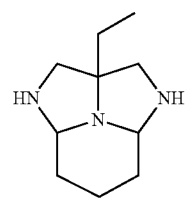 |

In some embodiments, the protected antimicrobial compound of formula I is 2a-methyloctahydro-1,4-dioxa-2a1-azacyclopenta[cd]indene. In some embodiments, the protected antimicrobial compound of formula I is (octahydro-1,4-dioxa-2a¹-azacyclopenta[cd]inden-2a-yl)methanol.

Compounds of formula I may be prepared, for example, as depicted in Scheme I. Typically, the antimicrobial aldehyde of interest (formaldehyde or glutaraldehyde) is mixed with multifunctional amine compound A in a suitable solvent, such as water. The mixture may be stirred and continued for sufficient time to allow the reaction to occur and the desired compound of formula I to form. The product may be used as is, or optionally further purified using techniques well known to those skilled in the art, such as crystallization, chromatography, distillation, etc.

SCHEME I formaldehyde or glutaraldehyde

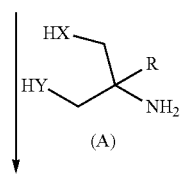

(A)

↓

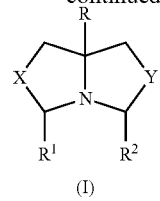

(I)

The compound A used in the synthesis described above is generally an amine compound that contains at least two additional functional groups comprised of hydroxyl(s), amine(s), or both. Examples include: 2-amino-2-methyl-1,3-propanediol, 2-amino-2-ethyl-1,3-propanediol, or tris(hydroxymethyl)aminomethane, 2-methyl-1,2,3-propanetriamine, and 2-ethyl-1,2,3-propanetriamine. Such compounds may be commercially available and/or may be readily prepared by those skilled in the art.

Some of the protected antimicrobial compounds of formula I are novel. Thus, in a further embodiment, the invention provides novel compounds of formula I. In some embodiments, the compound is 7a-methylhexahydro-1H-imidazo[1,5-c]imidazole. In some embodiments, the compound is 7a-ethylhexahydro-1H-imidazo[1,5-c]imidazole. In some embodiments, the compound is 2a-methyldecahydro-1,2a1,4-triazacyclopenta[cd]indene. In some embodiments, the compound is 2a-ethyldecahydro-1,2a1,4-triazacyclopenta[cd]indene.

The protected antimicrobial compounds described herein release antimicrobial aldehydes (formaldehyde or glutaraldehyde) when heat-activated. Unlike the free aldehydes, however, the protected compounds are more stable at elevated temperatures thus permitting extended control of microbial fouling. In addition, the protected compounds may exhibit improved stability in the presence of other chemical species that would otherwise degrade the free aldehydes, such as bisulfites, and amines.

Because of their stability and heat activation characteristics, the protected antimicrobial compounds of the invention are useful for controlling microorganisms for extended periods of time in aqueous or water-containing systems that are at elevated temperatures, including those that may be present or used in oil or natural gas applications, paper machine white water, industrial recirculating water, starch solutions, latex emulsions, hot rolling machining fluids, or industrial dishwashing or laundry fluids. In some embodiments, the aqueous or water-containing system may be present or used in oil or natural gas applications. Examples of such systems include, but are not limited to, fracturing fluids, drilling fluids, water flood systems, and oil field water.

In some embodiments, the aqueous or water-containing system may be at a temperature of 40° C. or greater, alternatively 55° C. or greater, alternatively 60° C. or greater, alternatively 70° C. or greater, or alternatively 80° C. or greater.

In addition to their heat stability, the compounds may further be effective when a deactivating agent, such as a source of bisulfite ion or amines is present in the system.

A person of ordinary skill in the art can readily determine, without undue experimentation, the concentration of the protected antimicrobial compound that should be used in any particular application. By way of illustration, a suitable concentration, based on the equivalent of antimicrobial aldehyde that is potentially released (assuming 100% release) by the protected compound is typically at least about 1 ppm, alternatively at least about 5 ppm, alternatively at least about 50 ppm, or alternatively at least about 100 ppm by weight. In some embodiments, the concentration is 2500 ppm or less, alternatively 1500 ppm or less, or alternatively 1000 ppm or less. In some embodiments, the aldehyde equivalent concentration is about 100 ppm.

The protected antimicrobial compounds may be used in the system with other additives such as, but not limited to, surfactants, ionic/nonionic polymers and scale and corrosion inhibitors, oxygen scavengers, nitrate or nitrite salts, and/or additional antimicrobial compounds.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism re-growth. In some embodiments, the microorganisms are bacteria. In some embodiments, the microorganisms are aerobic bacteria. In some embodiments, the microorganisms are anaerobic bacteria. In some embodiments, the microorganisms are sulfate reducing bacteria (SRB).

"Alkyl," as used in this specification encompasses straight and branched chain aliphatic groups having the indicated number of carbon atoms. Exemplary alkyl groups include, without limitation, methyl, ethyl, propyl, isopropyl, butyl, isobutyl, sec-butyl, tert-butyl, pentyl, and hexyl.

The following examples are illustrative of the invention but are not intended to limit its scope. Unless otherwise indicated, the ratios, percentages, parts, and the like used herein are by weight.

EXAMPLES

Example 1

Preparation of 2a-methyloctahydro-1,4-dioxa-2a1-azacyclopenta[cd]indene ("AMPD adduct")

Into a 4 oz glass jar equipped with a magnetic stirrer is added 2-amino-2-methyl-1,3-propanediol (AMPD) crystals (15.0 g, 0.143 mols), and water (10 g), which results in a slurry. The reaction is further cooled by an ice bath and held between 0 and 10° C. A 50% aqueous solution of glutaraldehyde (28.53 g, 0.143 mols) is slowly added over 30 mins by an addition funnel during which the color changes from colorless, to yellow, and finishes as a yellow green solution. The sample is stored at –20° C. and may be used as is, or it may be further purified.

The crude product solution may be purified by transferring it into a 250 ml round-bottomed flask (RBF) and concentrating it in vacuo on a rotary evaporator (roto-vap), which affords a semi-solid material (24.95 g, 103.5% yield). The product is dissolved into hot (70° C.) ethyl acetate (EtOAc, 50 ml), which is then decanted away from the polymeric material into a 250 ml round-bottomed flask (RBF). The polymeric residue is treated again with hot EtOAc (50 ml) and added to the 250 ml flask, but little additional material appears to dissolve. The insoluble green residue (4.33 g) is discarded.

The EtOAc solvent is removed in vacuo (30° C./0.5 torr) to afford a yellow-green oil (21.46 g, 89.1% yield). The oil is again dissolved into EtOAc (50 ml) and decanted away from the residue (0.6 g) and again the solvent removed to afford the product (20.1 g, 83.4% yield, 98.2% pure minus EtOAc peak). This material is transferred to a 65 ml RBF with a minimum amount of MeOH and is concentrated in vacuo (30° C./0.5 torr). The flask is fitted with a stir bar, a short path distillation apparatus with a thermometer and receiving flask (50 ml). Vacuum is applied and the mixture stirred as the hot water bath is warmed by a hot plate. The distillation sequence is shown in Table 1.

TABLE 1

| TIME (Clock) | POT TEMPERATURE (° C.) | HEAD TEMPERATURE (° C.) | VACUUM (torr) | COMMENTS |
|---|---|---|---|---|
| 1:15 | 40 | 25 | 1.3 | Warm from roto-vap |
| 1:20 | 60 | 25 | 0.7 | Some reflux |
| 1:25 | 56 | 42 | 0.5 | Fraction 1 ends (0.05 g) |
| 1:27 | 56 | 38 | 0.3 | Dry ice cools receiver |
| 1:45 | 80 | 61 | 0.25 | Distillate melted by hot air gun |
| 1:55 | 99 | 67 | 0.3 | Distillation slows |
| 2:00 | 97 | 57 | 0.25 | Distillation stops, thick orange oil in pot |

Distillation slows and stops even though there is a significant amount left in the pot which is found to be soluble in EtOAc. The clear, colorless overhead material (7.12 g, 29.5% yield, 99.7% purity) is melted and transferred into a 1 oz glass bottle, which results in a solid with a liquid layer on top (possibly from a small amount of decomposition). The bottle is inserted into a freeze-drying bottle that is attached to a vacuum pump (0.2 torr) to remove the liquid layer. This results in the isolation of the desired product as a colorless crystalline solid (6.66 g, 27.6% yield, 99.8% purity) whose melting point is determined to be 28.5-29.5° C. The product is confirmed by spectral analysis. GC/MS (CI mode) analysis shows [MH]$^+$ m/z 170. $^1$H NMR (ppm): 1.293 (s), 1.764-2.121 (m), 3.732 (q), 4.433 (s). $^{13}$C NMR (ppm): 2.135, 22.528, 38.110, 81.458, 89.461, 100.246.

Example 2

Preparation of (Octahydro-1,4-dioxa-2a$^1$-azacyclopentalcdlinden-2a-yl)methanol ("TA adduct")

Following the procedure of example 1 while making non-critical variations as needed, the title compound is prepared from glutaraldehyde and tris(hydroxymethyl)aminomethane (TA). The product is confirmed by spectral analysis. GC/MS (CI mode) analysis shows [MH]$^+$ m/z 186. 1HNMR (CD$_3$OD, ppm): 1.755-2.100 (m), 3.641 (s), 3.842 (q), 4.416 (s). 13C NMR (CD$_3$OD, ppm): 22.447, 38.110, 75.861, 85.591, 86.221, 100.833.

Example 3

Analysis of Glutaraldehyde Release

Samples of the AMPD-adduct and TA-adduct are analyzed for glutaraldehyde content. Samples are prepared in sterile deionized water at the molar equivalent of 2000 ppm glutaraldehyde. A standard of 500 ppm glutaraldehyde is also prepared. An initial measurement is taken just after sample preparation. Samples are then heat-aged at 55° C. for 2 h or 24 h and analyzed again. Glutaraldehyde concentration is measured directly via GC and after pre-column derivatization by HPLC. No glutaraldehyde is detected by GC. HPLC shows low levels of glutaraldehyde. These results are consistent with the reaction products being stable to elevated temperature but with slight degradation in the presence of the acidic conditions required for derivatization and HPLC analysis.

Example 4

Assay for Biocidal Efficacy

Purified adducts from Examples 1-2, adduct reaction mixtures ("crude adducts"), and the protective components alone (AMPD and TA) are tested for biocidal activity against a pool of aerobic organisms at room temperature and against sulfate reducing bacteria (SRB) at 40° C. Tests are performed as follows:

a. Aerobic Bacteria. A mixed pool of 6 bacterial species at approximately $5 \times 10^6$ CFU/mL in phosphate buffered saline is introduced into a 96-well plate (1 mL/well). Each well receives an independent chemical treatment (i.e. adduct, protective component, glutaraldehyde, etc. at varied concentrations). The remaining cell density in each well is then measured at given timepoints by dilution to extinction in a medium containing resazurin dye as an indicator.

It is found that none of the adducts or protective groups is biocidal at concentrations equivalent to up to 300 ppm glutaraldehyde by weight.

b. Thermophilic Bacteria. A 48-72 hour old culture of *T. thermophilus* is pelleted by centrifuging at 2000 g and the pellet resuspended in 10 times the culture volume of buffer (PBS or carbonate-buffered synthetic freshwater). The suspension is distributed into 10 mL aliquots in glass screw-cap tubes. Each tube is then treated with glutaraldehyde or an adduct and incubated at 70° C. At indicated timepoints, cell density in each tube is measured via dilution to extinction by serially diluting a sample and plating dilutions on solid media.

Results: (1) Samples treated with the equivalent of 100 ppm glutaraldehyde exhibit greater than 5-log lower CFU/mL than untreated samples after 24 h exposure to the adducts or glutaraldehyde. Subsequent re-challenging of the biocides by adding more bacteria also exhibits greater than 5-log reduction in CFU/mL after 24 h exposure. After 5 days, glutaraldehyde fails to control bacterial levels. In contrast, the AMPD-adduct and TA-adduct maintain greater than 5-log reduction in CFU/mL over the course of 18 days and 2 to 3-log reduction over 5 weeks.

(2) The experiment described above is repeated with lower concentrations of antimicrobial compound (equivalent to 50 ppm glutaraldehyde) and shorter exposure time (4 hr) between bacterial challenge and enumeration. In this case, glutaraldehyde and the AMPD and TA adducts maintained 4-log kill of the bacterial over 21 days with weekly challenges.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A method for reducing the quantity of microorganisms in an aqueous or water-containing system having a temperature of at least 40° C., the method comprising contacting the aqueous or water-containing system with a protected antimicrobial compound of the formula I:

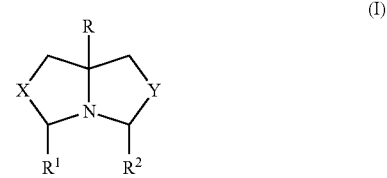

wherein R is $C_1$-$C_6$ alkyl optionally substituted with hydroxyl;

X and Y are independently O or NR" wherein R" is independently H or $C_1$-$C_6$ alkyl; and $R^1$ and $R^2$ are H or $R^1$ and $R^2$, together with the CH—N—CH group to which they are attached, form a piperidinyl ring.

2. A method according to claim 1 wherein X and Y are each O.

3. A method according to claim 1 wherein X and Y are each NH.

4. A method according to claim 1 wherein R is $C_1$-$C_3$ alkyl optionally substituted with one hydroxyl.

5. A method according to claim 1 wherein the compound of formula I is: 7a-methylhexahydro-1H-imidazo[1,5-c]imidazole; 7a-ethylhexahydro-1H-imidazo[1,5-c]imidazole; 2a-methyloctahydro-1,4-dioxa-2a1-azacyclopenta[cd]indene; 2a-ethyloctahydro-1,4-dioxa-2a1-azacyclopenta[cd]indene; (Octahydro-1,4-dioxa-2a'-azacyclopenta[cd]inden-2a-yl)methanol; 2a-methyldecahydro-1,2a-1,4-triazacyclopenta[cd]indene; 2a-ethyldecahydro-1,2a-1,4-triazacyclopenta[cd]indene; or a mixture of two or more thereof.

6. A method according to claim 1 wherein the aqueous or water-containing system is an oil or gas field fluid, a paper machine white water, an industrial recirculating water, a starch solution, a latex emulsion, a hot rolling machining fluid, or an industrial dishwashing or laundry fluid.

7. A method according to claim 1 wherein the aqueous or water-containing system is a fracturing fluid, a drilling fluid, a water flood system, or an oil field water.

8. A compound that is: 7a-methylhexahydro-1H-imidazo[1,5-c]imidazole; 7a-ethylhexahydro-1H-imidazo[1,5-c]imidazole; 2a-methyldecahydro-1,2a-1,4-triazacyclopenta[cd]indene; or 2a-ethyldecahydro-1,2a-1,4-triazacyclopenta[cd]indene.

* * * * *